US00PP14462P29

(12) United States Plant Patent
Pierce

(10) Patent No.: US PP14,462 P2
(45) Date of Patent: Jan. 13, 2004

(54) CALIBRACHOA PLANT NAMED 'CAL SCARED'

(50) Latin Name: *Calibrachoa* spp.
Varietal Denomination: Cal Scared

(75) Inventor: Robert Osteen Pierce, Watsonville, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/389,078
(22) Filed: Mar. 13, 2003
(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—A Para
(74) *Attorney, Agent, or Firm*—Jondle & Associates, PC

(57) ABSTRACT

'Cal Scared' is a new variety of Calibrachoa plant. This new variety has dark blue colored flowers.

1 Drawing Sheet

Genus and species: Calibrachoa spp.
Variety denomination: 'Cal Scared'.

BACKGROUND OF THE INVENTION

'Cal Scared' originated from a hybridization made in the year 2000 in Gilroy, Calif. The female parent was a Calibrachoa breeding line with lavender rose colored flowers known as 66-1, a carmine proprietary line unnamed and unpatented. The male parent was Calibrachoa variety 72-1, a rose proprietary line unnamed and unpatented.

'Cal Scared' is a product of a planned breeding program intended to create new calibrachoa plants with scarlet colored flowers, compact habit, good basal branching and moderately vigorous growth.

The new cultivar was created in 2000 in Gilroy, Calif. and has been asexually reproduced repeatedly by vegetative cuttings and tissue culture in Gilroy, Calif., Andijk, The Netherlands, and Guatemala over a 2-year period. The plant has also been trialed at Gilroy, Calif., Litchfield, Mich. and Andijk, The Netherlands. The present invention has been found to retain its distinctive characteristics through successive propagations; and this novelty is firmly fixed.

DESCRIPTION OF THE GENUS CALIBRACHOA LLAVE & LEX

The genus Petunia was originally established in 1803 by A. L. Jussieu, who described both *P. parviflora* and *P. nyctaginifloa* as type species. Using a non-horticultural system that selected the first mentioned species as the type species (lectotype), N. L. Britton and H. A. Brown declared *P. parviflora* as the type species for Petunia in 1913.

During the 1980's and 1990, H. J. Wijsman published a series of articles regarding the ancestry of *P. hybrida,* the Garden Petunia, and the inter-relationship of several species classified as Petunia. These studies discovered that *P. hybrida* and its ancestrial species, *P. nyctaginiflora* (=*P. axillaris*) and *P. violacea* (=*P. integrifolia*), possessed 14 pairs of chromosomes while several other species, including *P. parviflora*, possessed 18 pairs of chromosomes. Since *P. parviflora* was the lectotype species for the Petunia genus, Wijsman and J. H. de Jong proposed transferring the 14 chromosome species to the genus Stimoryne. Horticulturists opposed reclassifying the Garden Petunia and in 1986, Wijsman proposed the alternative of making *P. nyctaginiflora* the lectotype species for Petunia and transferring the 18 chromosome species to another genus. The I. N. G. Committee adopted this proposal. By 1990 Wijsman had transferred several species, including *P. parviflora* (=*C. parviflora*) to Calibrachoa, originally established by Llave and Lexarza in 1825. *Calibrachoa parviflora* (=*C. mexicana* Llave & Lexarza) is now the type species for the genus Calibrachoa.

Classification of the current Petunia and Calibrachoa species is still in progress. New species are also being identified. Consequently a proper description has not been written for the Calibrachoa genus. Calibrachoa can, however, be distinguished from Petunia based on the higher chromosome number, chromosome morphology, plant branching habit and type of flower bud aestivation. Whereas Petunia species bear a flower peduncle and one new stem from a node, Calibrachoa bear a flower peduncle and three stems. Petunia species have a cochlear corolla bud, a single outermost petal covers the other four, radially folded and terminally contorted petals. Calibrachoa flower buds are flat with all five petals linearly folded and the two lower petals forming a cover around the three other petals and fused together.

DETAILED DESCRIPTION OF THE NEW PLANT

The following traits and characteristics describe the new variety. The plant history was taken on 8 month old plants that were cut back numerous times prior to data readings being taken.

Classification:
- *Family.*—Solanaceae.
- *Species.*—Calibrachoa spp.

Growth:
- *Form.*—Semi upright and decumbent.
- *Habit.*—Good vigorous habit, well branched, full plant.
- *Height.*—10–20 cm.
- *Width.*—40–50 cm.
- *Time to produce a finished flowering plant.*—10–12 weeks.
- *Outdoors plant performance.*—Full sun, free flowering through the summer, some heat tolerance, used as a hanging plant, in mixed container plantings, mass planting in a bed.

*Time to initiate and develop roots.*—18–24 days.

*Rood description.*—White, fibrous.

Stems:

*Stem color.*—RHS 144B (yellow-green).

*Stem length.*—40–50 cm.

*Stem diameter.*—0.25 cm.

*Stem internodes length.*—0.7–1.3 cm.

*Stem texture.*—Many glandular hairs.

*Stem anthocyanin.*—Yes, in irregular patches on upper side.

*Pedicel color.*—RHS 144A (yellow-green).

*Pedicel length.*—2.5–3.0 cm.

*Pedicel diameter.*—0.1 cm.

*Pedicel texture.*—Many glandular hairs of various sizes.

Leaves:

*Arrangement.*—Alternate, upper leaves sub-opposite.

*Leaf color.*—Upper side, RHS 137A (green). Underside, RHS 138B (green).

*Leaf length.*—3.0–3.5 cm.

*Leaf width.*—0.8–1.3 cm.

*Leaf blade shape.*—Elliptic/Oblong.

*Leaf margin.*—Entire.

*Leaf apex aspect.*—Acute/Obtuse.

*Leaf bas aspect.*—Acuminate.

*Leaf texture.*—Many glandular hairs of various sizes.

*Venation.*—Palmate.

*Venation color.*—RHS 144A (yellow-green).

*Petiole color.*—RHS 144A (yellow-green).

*Petiole length.*—0.2–0.3 cm.

*Petiole diameter.*—0.2 cm.

*Petiole texture.*—Many glandular hairs of various sizes.

Bud:

*Color at tight bud.*—RHS 84B (violet).

*Bud shape.*—Oblong.

*Bud diameter.*—0.4 cm.

*Bud length.*—2.0–2.3 cm.

Flowers:

*Blooming habit.*—Continuous throughout the growing season. Good floriferousness.

*Inflorescence type.*—Flowers solitary in upper leaf axis.

*Floret type.*—Funnel form, 5 lobed petals, fused at base.

*Young flower color.*—Closest to RHS 46B (red) base color and velvety looking; RHS 187A (greyed-purple) mid-veins and slight edging on the margin; RHS 6A (yellow) throat.

*Young flower floret diameter.*—2.5–28 cm.

*Mature flower color.*—Front side, RHS 44A (red) and RHS 42A (red) base mingled base color, with a hint of RHS 45C (red) at and around the margins; RHS 178A (greyed-red) mid-veins.

*Mature flower color.*—Underside, a little lighter than RHS 180D (greyed-red) base color, with irregular patches of RHS 51B (red); RHS 200B (brown) mid-veins.

*Corolla tube color inside.*—RHS 6A (yellow) base color; RHS 199A (greyed-brown) mid-veins and secondary veins.

*Corolla tube length.*—1.7–1.9 cm.

*Corolla outside texture.*—Many glandular hairs various sizes.

*Flower (limb) diameter.*—2.8–3.0 cm.

*Petal apex shape.*—Retuse.

*Petal base shape.*—Fused.

*Petal margin.*—Entire.

*Waviness of petals.*—None.

*Petal lobation.*—Weak to moderate.

*Petal texture.*—Papillose and velvety looking.

*Sepals.*—5, fused at the base.

*Sepal color.*—RHS 137A (green).

*Sepal length.*—1.3–1.5 cm.

*Sepal width.*—0.3–0.35 cm.

*Sepal shape.*—Oblong.

*Sepal apex.*—Acute.

*Sepal texture.*—Many glandular hairs of various sizes.

*Lastingness of individual blooms.*—4–8 days.

*Fragrance.*—None.

Reproductive organs:

*Stamens.*—5, 2 taller, 2 shorter, 1 very short.

*Filament color.*—RHS 154D (yellow-green).

*Pollen color.*—RHS 13B (yellow).

*Pistil.*—One.

*Stigma color.*—RHS 145A (yellow-green).

*Style color.*—RHS 154D (yellow-green).

*Fruit seed set.*—Not observed.

DISEASE AND INSECT RESISTANCE

Not observed.

COMPARISON WITH MOST SIMILAR VARIETY

'Cal Scared' differs from the female parent 66-1 in the following ways: 'Cal Scared' has scarlet colored flowers and 66-1 has carmine colored flowers. 'Cal Scared' has larger flowers and larger leaves than 66-1.

'Cal Scared' differs from the male parent 72-1 in the following ways: 'Cal Scared' has scarlet colored flowers than 72-1 has rose-colored flowers. 'Cal Scared' flowers are less prostrate in habit and have more basal branching than 72-1.

What is claimed is:

1. A new and distinct Calibrachoa plant as shown and described herein.

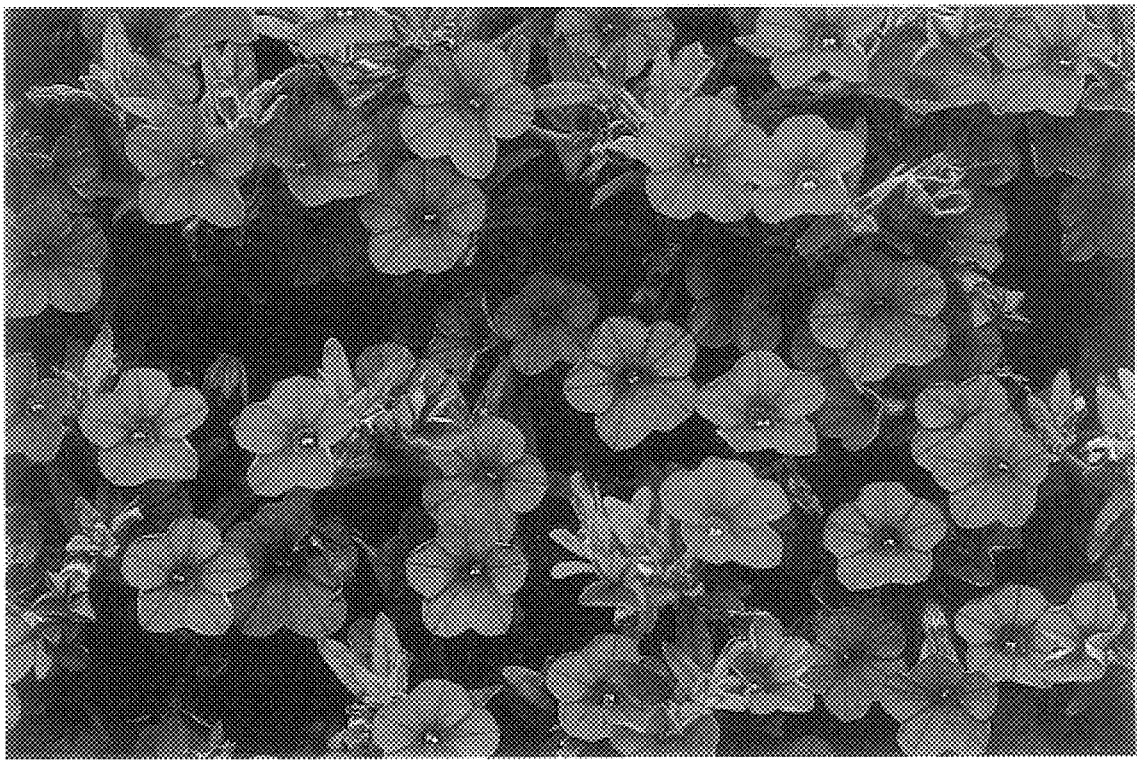

* * * * *